US006419640B1

(12) United States Patent
Taylor

(10) Patent No.: US 6,419,640 B1
(45) Date of Patent: Jul. 16, 2002

(54) MULTIPLE-SPECIMEN, ENDOSCOPIC BIOPSY FORCEPS

(76) Inventor: Thomas V. Taylor, 1806 Vassar, Houston, TX (US) 77098

( * ) Notice: Subject to any disclaimer, the term of this patent is extended or adjusted under 35 U.S.C. 154(b) by 8 days.

(21) Appl. No.: 09/678,268

(22) Filed: Oct. 3, 2000

(51) Int. Cl.$^7$ ............................................... A61B 10/00
(52) U.S. Cl. ...................................... 600/564; 606/205
(58) Field of Search ................................ 600/564, 565, 600/566, 567, 568, 569, 570, 571, 572; 606/205, 206, 207, 208, 209

(56) References Cited

U.S. PATENT DOCUMENTS

| | | |
|---|---|---|
| 3,924,608 A | 12/1975 | Mitsui |
| 4,427,014 A | 1/1984 | Bel et al. |
| 4,817,630 A | 4/1989 | Schintgen et al. |
| 5,052,402 A | 10/1991 | Bencini et al. |
| 5,195,533 A | 3/1993 | Chin et al. |
| 5,238,002 A * | 8/1993 | Devlin et al. ............... 600/564 |
| 5,318,589 A | 6/1994 | Lichtman |
| 5,385,570 A | 1/1995 | Chin et al. |
| 5,562,102 A | 10/1996 | Taylor |

* cited by examiner

Primary Examiner—Kevin Shaver
Assistant Examiner—Pamela Wingood
(74) Attorney, Agent, or Firm—Daniel N. Lundeen; Lundeen & Arismendi, LLP

(57) ABSTRACT

A biopsy forceps for obtaining multiple tissue specimens of an organ through a biopsy channel of an endoscope is disclosed. The biopsy forceps comprises a tubular body, a central wire, a set of jaws, and an activating handle. The central wire is disposed in the tubular body with the distal end of the central wire extending therethrough. A set of jaws is cooperatively mounted to the distal end of the central wire such that as the central wire is displaced by the activating handle, the distal end of the central wire is drawn toward the tubular body, which forces the jaws to close. A space is provided between the wire and the housing for retaining multiple tissue specimens.

12 Claims, 5 Drawing Sheets

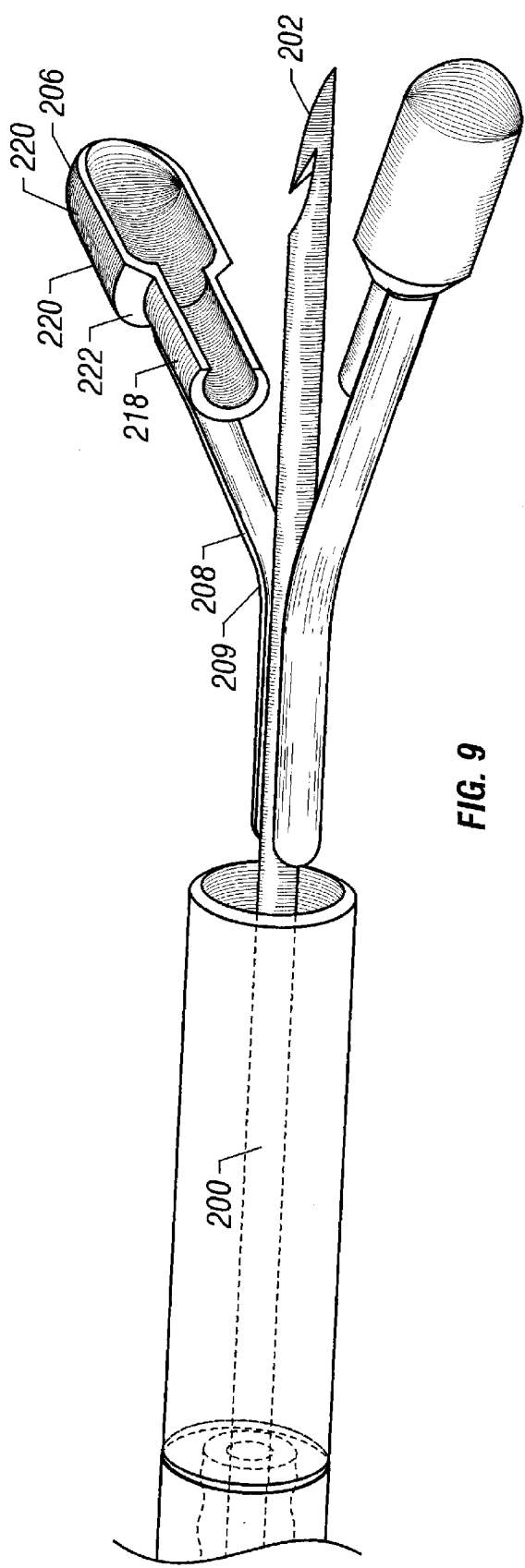
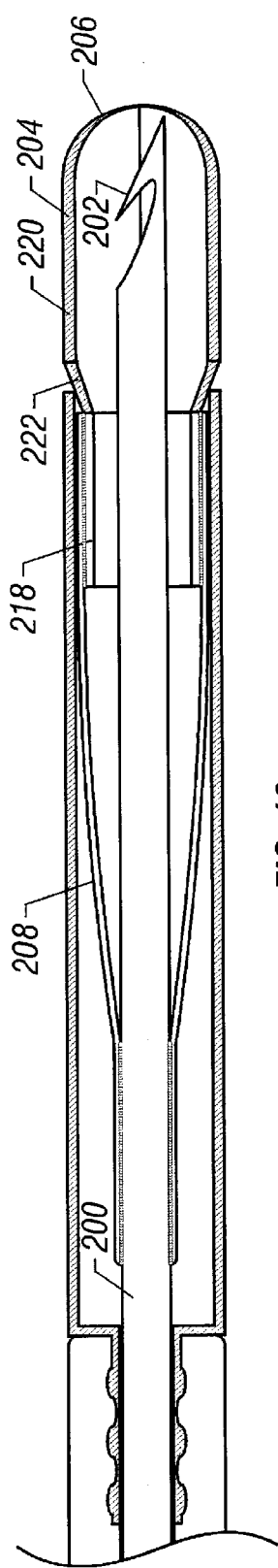

MULTIPLE-SPECIMEN, ENDOSCOPIC BIOPSY FORCEPS

FIELD OF THE INVENTION

This invention relates to a biopsy forceps and, more specifically, to a biopsy forceps capable of obtaining multiple tissue samples in a single passage through an endoscope.

BACKGROUND OF THE INVENTION

Gastroenterologists, surgeons, and other physicians commonly obtain tissue samples for biopsy when examining interior parts of the body using an endoscope. Modern endoscopes are usually flexible instruments comprising a fiber optic viewing system and a tubular channel through which biopsy forceps can be passed to obtain the samples. Some prior art biopsy forceps are designed to obtain a single small piece of tissue on each passage through the endoscope. Such single pass forceps, however, are time consuming to use since clinicians frequently require multiple biopsies of a diseased area in order to gather adequate pathological or other scientific information. The instrument must be passed in and out of the endoscope for each biopsy specimen.

In my earlier U.S. Pat. No. 5,562,102, I disclosed an endoscopic multiple biopsy forceps in which specimen-taking jaws were operated independently of a central specimen transfixing stylet or wire. I have now devised a multiple biopsy forceps in which the jaws and stylet cooperate to obtain and retain the multiple tissue specimens with a simplified operation.

SUMMARY OF THE INVENTION

A preferred embodiment of the present invention provides a biopsy forceps for obtaining multiple tissue specimens of an organ through a biopsy channel of an endoscope. The biopsy forceps comprises a tubular body, a tubular housing, a central wire, a set of jaws, and an activating handle. The tubular body has a length and an outside diameter for passage through the biopsy channel. The tubular housing is affixed to the tubular body or forms the distal end of the tubular body. A central wire is disposed in the tubular body with the distal end of the central wire extending through the tubular housing. The distal end of the central wire has a barbed spike for penetrating tissue. A set of jaws is cooperatively mounted to the distal end of the central wire. A proximal activating handle displaces the central wire such that as the distal end of the central wire is drawn toward the tubular housing, the tubular housing forces the jaws to close. A space is provided between the wire and the jaws for retaining multiple tissue specimens transfixed by the wire.

Another preferred embodiment of the present invention provides a method for obtaining multiple tissue biopsies of an organ through an endoscope with the above-mentioned forceps. The endoscope has a biopsy channel and is inserted to visualize an area to be biopsied. The biopsy forceps are inserted through the biopsy channel. The barbed spike of the central wire is placed in penetrating contact with the tissue to be biopsied. The central wire is withdrawn into the tubular housing, which forces the jaws to grasp a sample of the tissue to be biopsied. The grasped tissue is retained on the central wire in the space between the jaws and the wire. The same steps are repeated to sequentially collect tissue samples in the space along the central wire. Withdrawing the biopsy forceps from the biopsy channel retrieves the tissue samples.

BRIEF DESCRIPTION OF THE DRAWINGS

FIG. 9 is an enlarged perspective view of a distal end of a further alternate embodiment of a multiple biopsy forceps of the present invention shown in an open position ready for sample collection.

FIG. 10 is a cross-sectional view of the distal end of the multiple biopsy forceps of FIG. 9 shown in a closed position corresponding to sample collection.

DETAILED DESCRIPTION OF THE INVENTION

Figure 1:
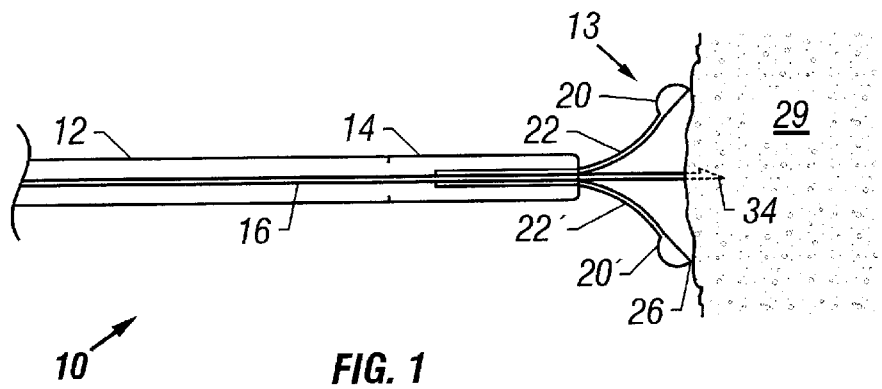
FIG. 1 is a side sectional view of the distal end of a multiple biopsy forceps of one embodiment of the present invention showing a needle having a barbed retaining element that has penetrated the tissue wall, and showing the relative positions of the tubular housing and the jaws.
Figure 2:
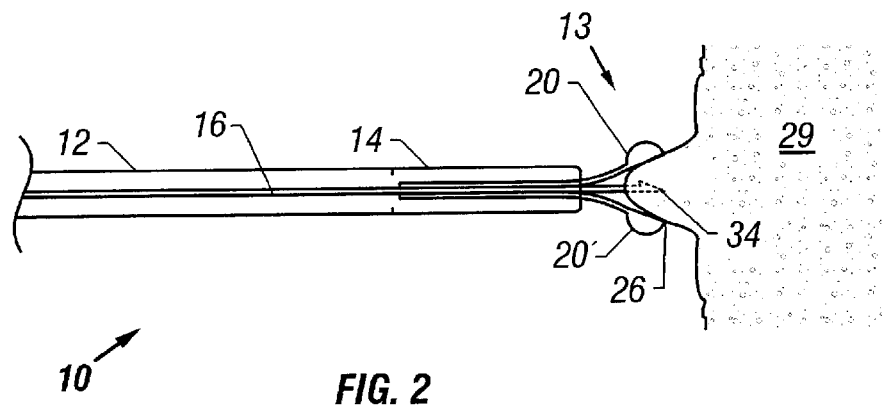
FIG. 2 is a side sectional view of the distal end of the multiple biopsy forceps of FIG. 1 showing the jaws gathering a tissue sample. Also shown is the relative position of the tubular housing as the jaws gather the sample.
Figure 3:
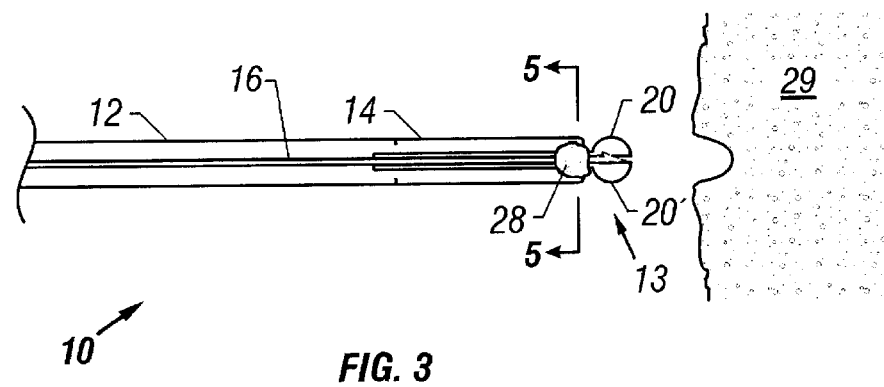
FIG. 3 is side sectional view of the distal end of the multiple biopsy forceps of FIGS. 1–2 shown with the jaws closed around the tissue sample subsequent to removing the sample from the organ wall.
Figure 4:
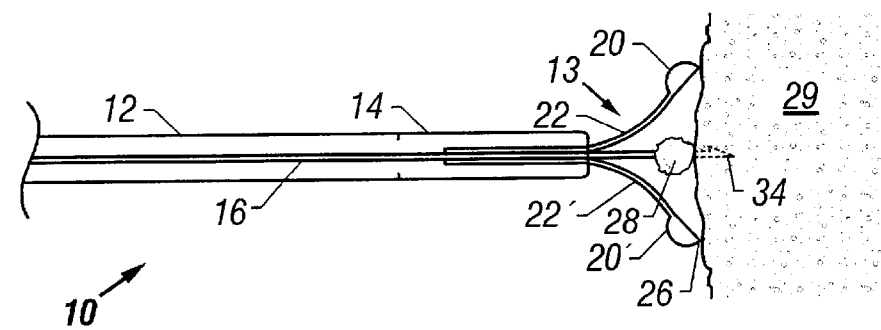
FIG. 4 is a side sectional view of the distal end of the multiple biopsy forceps of FIGS. 1–3 shown with an initial sample obtained and the tissue wall again penetrated by the barbed retaining element to initiate gathering of a subsequent, specimen.
Figure 5:
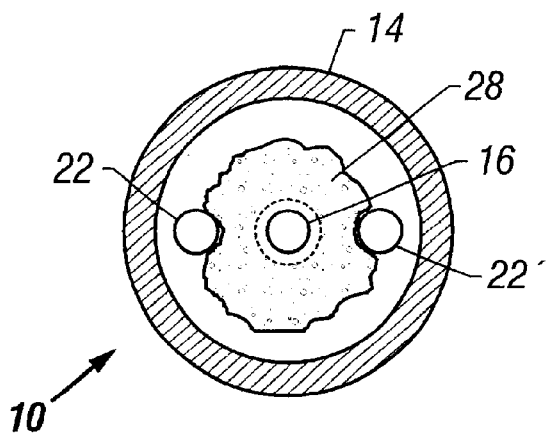
FIG. 5 is a cross-sectional view of the multiple biopsy forceps of the present invention as seen along the lines 5–5 in FIG. 3.
Figure 6:
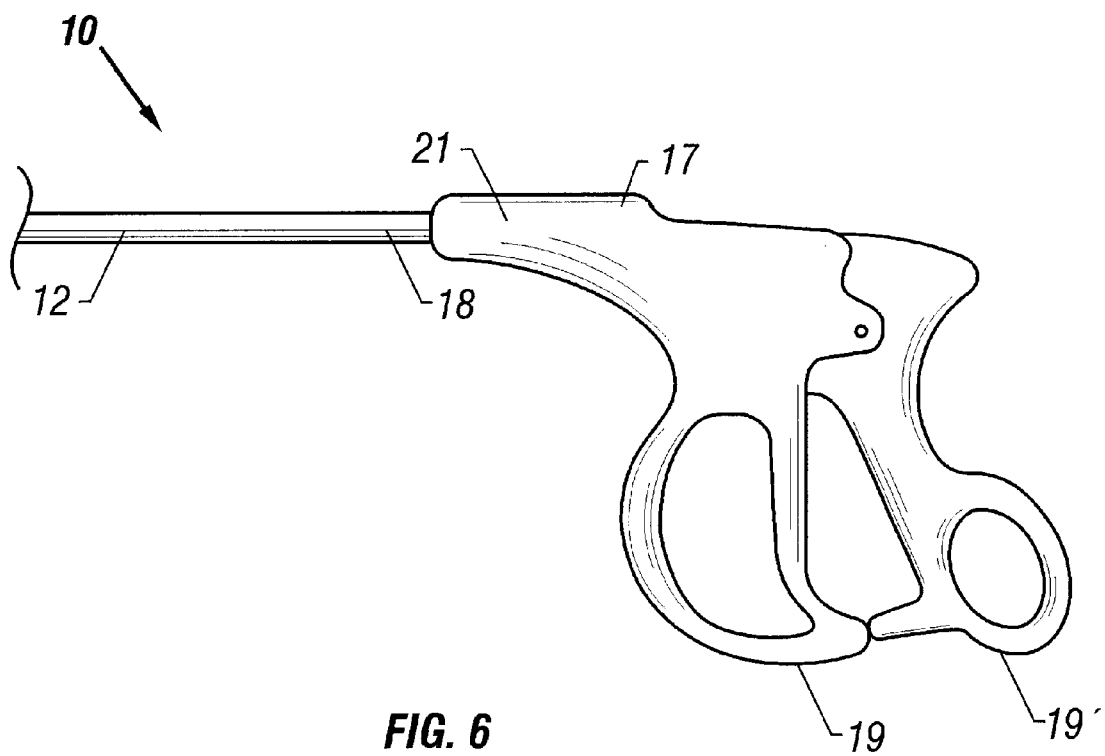
FIG. 6 is a schematic side view of a proximal end of the multiple biopsy forceps of FIGS. 1–5 showing the activating handle.

The multiple biopsy forceps of the present invention are suitable for use with an endoscope and permit the clinician to obtain necessary tissue samples for biopsy and specimen analysis with a single pass through the endoscope. Use of the present forceps can reduce equipment usage and operating time for biopsy procedures, and reduce patient discomfort.

Referring to FIGS. 1–6, wherein like numerals reference like elements, the forceps 10 of the present invention is a flexible, tubular medical instrument suitable for being passed down a conventional biopsy channel of an endoscope (not shown). The forceps 10 can be used to obtain multiple tissue samples per pass for biopsy of a potentially diseased tissue observed using the endoscope. The endoscope, as is well known in the art, generally comprises a tubular body having an annular biopsy channel for the biopsy forceps and a fiber optic cable for viewing the interior regions of the body. The endoscope is typically passed down the pharynx or up through the rectum to observe the interior regions of the gastrointestinal tract. If a biopsy is needed, the medical practitioner then inserts the biopsy forceps through the biopsy channel.

To effect slideable insertion through the biopsy channel, the forceps 10 comprises a flexible, tubular body 12 having a suitable length and outside diameter. The tubular body 12 terminates at its distal end in a tubular housing 14.

A central wire 16 is disposed in the tubular body 12 and extends from the proximal end 18 of the tubular body 12 through the tubular housing 14. Relative position of the central wire 16 with respect to the tubular housing 14 is effected by a scissor-type handle 17 disposed at the proximal end of the forceps 10 (see FIG. 6), or alternatively by a conventional plunger-type mechanism (not shown). The construction and operation of such a proximal handle 17 is well known in the art. Generally, the handle 17 comprises two pivotably coupled, hand operated legs 19, 19' having a distal end 21 attached to the proximal end 18 of the tubular body 12 and the central wire 16 (not shown) respectively. Manipulation of the handle 17 pivots the legs 19, 19' and imparts a change of position at respective distal ends 21. Pivoting of the ends 21, in turn, imparts a relative longitudinal position change of the central wire 16 and the tubular body 12 with respect to each other. Such change determines the distance the central wire 16 extends from the tubular housing 14 at the distal end of the wire 16.

A set of jaws 13 is mounted near the distal end of the central wire 16. The jaws 13 comprise upper and lower cusps 20, 20' on distal ends of hinged arms 22, 22' under spring tension so that the cusps 20, 20' have an open bias. The jaws 13 are typically made of a metallic material such as stainless steel to impart a spring bias to the cusps 20, 20' or a ceramic material. The jaws 13 have a mouth suitable for grasping a tissue sample 28 for biopsy from an organ wall 29 when the jaws 13 are closed.

Longitudinally drawing the distal end of the central wire 16 toward the tubular housing 14 by operation of the scissor-type handle 17 draws the jaws 13 into the tubular housing 14, which in turn exerts sufficient force on the spring biased arms 22, 22' and cusps 20, 20' to effect closure of the jaws 13. Thus, the jaws 13 are in cooperative engagement with the central wire 16.

The distal end of the central wire 16 terminates in a barbed spike 34 suitable for puncturing the organ wall 29 and engaging the organ wall 29. The jaws 13 can serve as a stop to prevent the spike 34 from overpenetrating the organ wall 29. When the central wire 16 is drawn towards the proximal end 18 of the tubular body 12, the barbed spike 34 pulls a sample section of the organ wall 29 toward the cusps 20, 20' of the jaws 13. As the central wire 16 continues to be withdrawn, the tubular housing 14 acts to close the cusps 20, 20' around the sample 28 for tearing or cutting, and the sample 28 is separated from the organ wall 29.

The spike 34 at the distal end of the central wire 16 acts as a retaining element suitable for retaining a plurality of tissue samples 28 acquired by repeated use of the forceps 10 during a single pass through the endoscope. Each subsequent sample 28 forces the previous sample 28 along the central wire 16 toward the tubular housing 14. Thus, several samples 28 can be obtained on each pass of the forceps 10. A sample retention space is provided between the spike 34 and the fulcrum of the jaws 13 by forming a hollowed out space in the cusps 20, 20' and/or in the arms of the jaws 13. Alternatively or additionally, the arms 22, 22' of the jaws 13 can be thin so as to create a radial space between the respective arms of the jaws 13.

The multiple biopsy forceps 10 of the present invention can be made to be disposable. The tubular body 12 can be made of a rigid but flexible plastic such as polypropylene, polyethylene, polyacrylic, and the like or a metallic material, so that the diameter of the body 12 is rigid for good slideability, but flexible along the length for ease of passage through the endoscope, especially when acutely angled. For laparoscopic applications, the tubular body 12 is preferably rigid.

To use the biopsy forceps of the present invention to take multiple specimens for biopsy per passage through the endoscope, the clinician, once having inserted the endoscope into the patient and observed diseased tissue for biopsy, then inserts the present forceps 10 through the endoscope biopsy channel. The endoscope is used to guide the central wire 16 of the forceps 10 to the organ tissue to be biopsied. An adjustment of the position of the central wire 16 can be made either by manipulating the length of the endoscope in the patient or the tubular body 12 in the endoscope channel.

Once the central wire 16 is positioned approximate the tissue to be biopsied, the barbed spike 34 is forced to penetrate the organ wall 29. The handle 17 is then operated to pull the barbed spike 34 of the central wire 16 back toward the tubular housing 14. This acts to simultaneously pull a sample 28 from the organ wall 29 and close the jaws 13 around a sample 28 of the tissue. If necessary, a slight tug on the tubular body 12 of the forceps 10 tears the sample 28 from the organ wall 29. Another sample(s) can be taken by repeating the steps detailed above. It should be understood that samples 28 previously collected are forced serially rearward on the central wire 16 upon the collection of subsequent samples 28.

When no additional biopsy samples are required or the collection space on the wire is filled to capacity, the forceps is removed from the endoscope biopsy channel and the tissue samples 28 are removed from the central wire 16 and catalogued to the area 29 of the organ tissue sampled. Between patients, a used disposable forceps should be properly disposed of and used non-disposable forceps should be sterilized.

Figure 7:
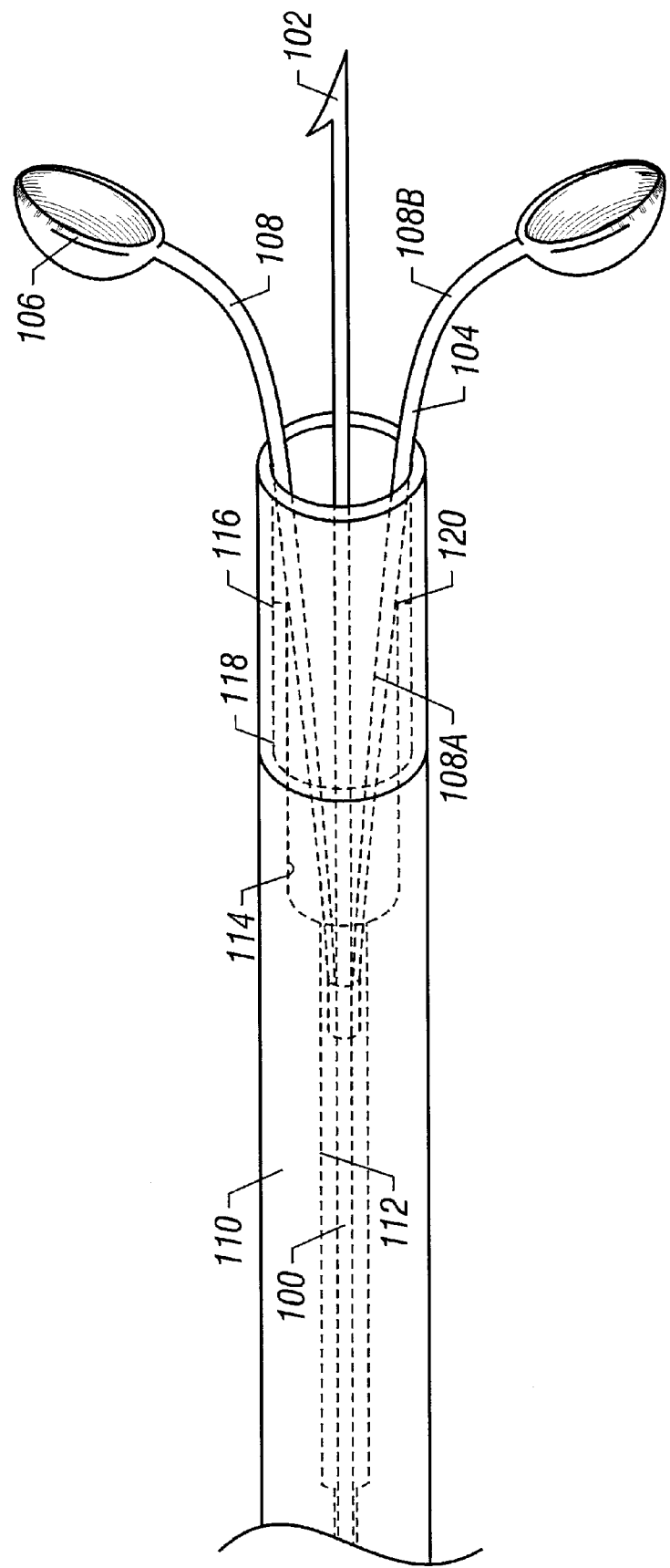
FIG. 7 is an enlarged perspective view of a distal end of another embodiment of the multiple biopsy forceps of the invention.
Figure 8:
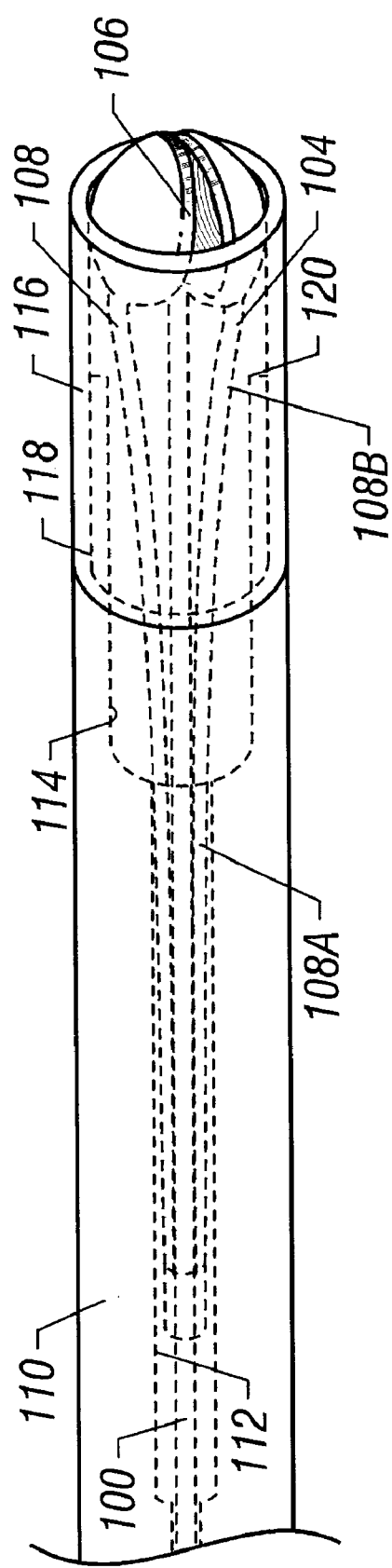
FIG. 8 is an enlarged perspective view of the forceps of FIG. 7 shown in a closed position corresponding to sample collection.

Another alternate embodiment of the present invention is seen in FIGS. 7–8. A central stylet 100 has a barbed tip 102 at its distal end. The stylet 100 preferably has a uniform diameter behind the tip 102. The jaws 104 have cusps 106 that terminate on distal ends of the arms 108. The arms 108 are preferably formed of a memory metal, each arm 108 attached at a proximal end to the stylet 100 and having a curvature that increases toward the cusps 106 so as to open the jaws 104 away from the tip 102. Preferably, the arms 108 have a straight or flared section 108A between the stylet 100 and the curved section 108B adjacent the cusps 106, and allow the tip 102 to be advanced ahead of the jaws 104 to permit primary fixation of the barbed tip 102 in the tissue to be biopsied.

The housing 110 is a flexible plastic tube that has a main central channel 112 for slideably receiving the stylet 100 and the arms 108 of the jaws 104, and an enlarged intermediate channel 114 that allows the outwardly biased arms 108 to flare outwardly toward a memory position. A tubular tip 116 can circumscribe the proximal end of the housing 110, made of metal or another suitable material for reinforcement and better wear characteristics for bearing against the outer surfaces of the arms 108 and cusps 106. The tubular tip 116 preferably has the same outside diameter as the remainder of the housing 110. The housing 110 has a slightly reduced outside diameter 118 under the tubular tip 116 to slideably receive the inside diameter of the tubular tip 116 which is securely fixed thereto. The tubular tip 116 can preferably extend beyond the distal end 120 of the housing 110 to form a generally approximate frustoconical surface with the termini of the intermediate channel 114 and the main central channel 112. The cusps 106 are dimensioned, i.e. they have a thickness, so as to firmly cut and/or grasp the tissue for tearing at least at the very distal end thereof when drawn inside the tip 116.

In operation, the surgeon positions and advances the tip 102 into the tissue to be sampled with the jaws 104 in a relatively open position. Entry of the tip 102 into the tissue pushes any previous specimens transfixed on the stylet 100 farther up the stylet 100 along the uniform diameter thereof away from the tip 102. As the housing 110 is then advanced along the stylet 100 by, for example, manipulation of the distal handle 17 (see FIG. 6), the jaws 104 are closed to force the cusps 106 into an opposing cutting or tearing position on either side of the tissue sample around the tip 102. The arms 108 are generally bowed outwardly near their attachment to the cusps 106 within the tip 116 around any specimen(s) previously transfixed on the stylet 100. If necessary, a tearing motion can be used to sever the tissue specimen held on the tip 102 between the cusps 106. After the specimen is removed from the in vivo tissue, the device may be withdrawn, or if additional specimens are to be obtained, the jaws 104 pushed out of the housing 110 by appropriate manipulation of the handle 17 (FIG. 6) for repetition of the sample gathering procedure at a new tissue site.

A further alternate embodiment of the present invention is seen in FIGS. 9–10. A central stylet 200 terminates in a barbed tip 202 formed in its distal end. The stylet 200 preferably has a uniform diameter behind the tip 202. The jaws 204 have cusps 206 that terminate on distal ends of the arms 208. The arms 208 are preferably formed of a memory metal, each arm 208 attached at a proximal end to the stylet 200 and having a curvature or bend at 209 so as to open the jaws 204 away from the tip 202. Preferably, the bend 209 allows the tip 202 to be advanced ahead of the jaws 204 to permit primary fixation of the barbed tip 202 in the tissue to be biopsied. The jaws 204 can be fabricated by stamping or molding, and welding or crimping the fulcrum of the jaws 204 to the stylet 200.

The housing 210 is a flexible plastic tube that has a central channel 212 for slideably receiving the stylet 200. A distal end of the housing 210 receives a nipple 215 extending proximally from a generally tubular tip 216, which is preferably made of a metallic material such as stainless steel. The central channel 212 presents an inside diameter that frictionally engages an outside diameter of the nipple 215 to securely hold the tubular tip 216.

The tubular tip 216 has a large inside diameter relative to the stylet 200. The cusps 206 have a proximal portion 218 having an outside diameter just smaller than an inside diameter of the tubular tip 216 to allow it to be drawn inside the tip 216, with sufficient clearance to accommodate the arms 208 that are secured by welding or the like to the outside surface of the proximal portion 218. The distal portion 220 has a relatively larger outside diameter, relative to proximal portion 218, that is joined by a frustoconical portion 222. The bearing of the frustoconical portion 222 against the distal end of the tubular tip 216 facilitates closure of the cusps 206 as they are drawn inside the tubular tip 216 so as to allow the tissue specimen to be grasped for tearing or cutting by the cusps 206. The inside diameter of the distal portion 220, and preferably also inside diameter of the proximal portion 218, are relatively larger than the diameter of the stylet 200 so as to allow sufficient space for retention and storage of multiple specimens transfixed on the stylet 200.

In operation, the surgeon positions and advances the tip 202 into the tissue to be sampled with the jaws 204 in a relatively open position. Entry of the tip 202 into the tissue pushes any previous specimens transfixed on the stylet 200 farther up the stylet 200 along the uniform diameter thereof away from the tip 202. As the housing 210 is then advanced along the stylet 200 by, for example, manipulation of the distal handle 17 (see FIG. 6), the jaws 204 are closed to force the cusps 206 into an opposing cutting or tearing position on either side of the tissue sample around the tip 202. If necessary, a tearing or tugging motion can be used to help sever the tissue specimen held on the tip, 202 between the cusps 206. After the specimen is removed from the in vivo tissue, the device may be withdrawn, or if additional specimens are to be obtained, the jaws 204 are pushed back out of the tubular tip 216 by appropriate manipulation of the handle 17 (FIG. 6) for repetition of the sample gathering procedure at a new tissue site.

The foregoing description of the invention is illustrative and explanatory thereof. Various changes in the materials, apparatus, and particular parts employed will occur to those skilled in the art. It is intended that all such variations within the scope and spirit of the appended claims be embraced thereby.

What is claimed is:

1. A method for obtaining multiple tissue biopsies of an organ through an endoscope, the method comprising the sequential steps of:

(a) inserting an endoscope having a biopsy channel to visualize an area to be biopsied;

(b) nserting a biopsy forceps through the biopsy channel, the biopsy forceps comprising:

a tubular body having a length and outside diameter for passage through the biopsy channel;

a tubular housing affixed to the tubular body;

a central wire disposed in the tubular body with the distal end of the central wire extending through the tubular housing, the distal end of the central wire having a barbed spike for penetrating tissue of an organ;

a set of jaws cooperatively mounted to the distal end of the central wire;

a proximal activating handle for displacing the central wire such that as the distal end of the central wire is drawn toward the tubular housing, the tubular housing forces the jaws to close;

(c) placing the barbed spike of the central wire in penetrating contact with the tissue to be biopsied;

(d) withdrawing the central wire, forcing the jaws to grasp a sample of the tissue to be biopsied;

(e) retaining the grasped tissue on the central wire;

(f) repeating steps (c) through (e) to sequentially collect tissue samples on the central wire;

(g) withdrawing the biopsy forceps from the biopsy channel to retrieve the tissue samples.

2. The method of claim 1, further comprising disposing of the forceps.

3. The method of claim 1, further comprising sterilizing the forceps for reuse.

4. The method of claim 1 wherein the tubular housing of the forceps forms the distal end of the tubular body.

5. The method of claim 1 wherein the tubular body of the forceps is made of a substantially rigid plastic material, which is flexible along the biopsy channel of the endoscope.

6. The method of claim 1 wherein the jaws of the forceps are cusp shaped, include cutting edge and are made from a metallic or ceramic material.

7. The method of claim 1 wherein the forceps comprise a space between the central wire and the housing for retaining the sequentially collected tissue specimens.

8. A biopsy forceps for obtaining multiple tissue specimens of an organ through a biopsy channel of an endoscope, comprising:

a tubular body having a length and outside diameter for passage through the biopsy channel;

a tubular housing affixed to the tubular body;

a central wire disposed in the tubular body with the distal end to the central wire extending through the tubular housing, the distal end of the central wire having a barbed spike for penetrating tissue of an organ;

a set of jaws cooperatively mounted to the distal end of the central wire;

a proximal activating handle for displacing the central wire such that as the distal end of the central wire is drawn toward the tubular housing, the tubular housing forces the jaws to close;

a space between the central wire and the housing for retaining multiple tissue specimens.

9. The forceps of claim 8 made of a disposable material.

10. The forceps of claim 8 wherein the tubular housing forms the distal end of the tubular body.

11. The forceps of claim 8, wherein the tubular body is made of a substantially rigid plastic material, which is flexible along the biopsy channel of the endoscope.

12. The forceps of claim 8, wherein the Jaws are cusp shaped, include a cutting edge and are made from a metallic or ceramic material.

* * * * *